US012611098B2

(12) United States Patent
Hendargo

(10) Patent No.: US 12,611,098 B2
(45) Date of Patent: Apr. 28, 2026

(54) CONTROL SYSTEM FOR OCT IMAGING, OCT IMAGING SYSTEM AND METHOD FOR OCT IMAGING

(71) Applicant: Leica Microsystems NC, Inc., Durham, NC (US)

(72) Inventor: Hansford Hendargo, Durham, NC (US)

(73) Assignee: LEICA MICROSYSTEMS NC, INC., Durham, NC (US)

( * ) Notice: Subject to any disclaimer, the term of this patent is extended or adjusted under 35 U.S.C. 154(b) by 404 days.

(21) Appl. No.: 18/253,604

(22) PCT Filed: Nov. 18, 2021

(86) PCT No.: PCT/EP2021/082152
§ 371 (c)(1),
(2) Date: May 19, 2023

(87) PCT Pub. No.: WO2022/106544
PCT Pub. Date: May 27, 2022

(65) Prior Publication Data
US 2023/0414096 A1 Dec. 28, 2023

Related U.S. Application Data

(60) Provisional application No. 63/115,637, filed on Nov. 19, 2020.

(51) Int. Cl.
*A61B 3/10* (2006.01)
*A61B 3/15* (2006.01)

(52) U.S. Cl.
CPC .............. *A61B 3/102* (2013.01); *A61B 3/152* (2013.01)

(58) Field of Classification Search
CPC ..... A61B 3/102; A61B 3/0025; A61B 5/0066; A61B 3/12; A61B 3/14; A61B 3/152; (Continued)

(56) References Cited

U.S. PATENT DOCUMENTS 7,349,098 B2 3/2008 Li
8,939,582 B1 1/2015 Spaide et al.
(Continued)

FOREIGN PATENT DOCUMENTS

JP 2014/509544 A 4/2014
JP 2015/016290 A 1/2015
(Continued)

*Primary Examiner* — Brandi N Thomas
(74) *Attorney, Agent, or Firm* — LEYDIG, VOIT & MAYER, LTD.

(57) ABSTRACT

The invention relates to a control system (130) for controlling optical coherence tomography imaging means for imaging a subject (190), the control system being configured to perform the following steps: receiving scan data (122) from the subject (190) being acquired by means of optical coherence tomography, performing data processing on the scan data (122), and obtaining image data (142) for an image (144) of the subject, and the processing system (130) further being configured to adapting, based on a change of a value, the value characterizing an axial position (z) of the subject (190) with respect to the OCT imaging means, between two sets of image data, at least one parameter of the OCT imaging means, to a processing system, to an OCT imaging system (100) and a corresponding method.

15 Claims, 3 Drawing Sheets

(58) Field of Classification Search
CPC .................. A61B 3/113; A61B 3/0058; G06T
2207/10101; G06T 2207/30041; G06T
2207/20081; G06T 5/60
See application file for complete search history.

(56)                        References Cited

U.S. PATENT DOCUMENTS

| | | |
|---|---|---|
| 10,092,178 B2 | 10/2018 | Narasimha-Iyer et al. |
| 11,071,449 B2 | 7/2021 | Heeren |
| 11,328,417 B2 | 5/2022 | Yabusaki |
| 2015/0359425 A1 | 12/2015 | Hathaway et al. |
| 2016/0040977 A1 | 2/2016 | An et al. |
| 2020/0085292 A1 | 3/2020 | Fukuma et al. |
| 2020/0093364 A1* | 3/2020 | Hirose .................. A61B 3/102 |

FOREIGN PATENT DOCUMENTS

| | | |
|---|---|---|
| JP | 2019/511273 A | 4/2019 |
| JP | 202058800 A | 4/2020 |
| JP | 2021/119973 A | 8/2021 |
| WO | WO 2019/088020 A1 | 5/2019 |

* cited by examiner

CONTROL SYSTEM FOR OCT IMAGING, OCT IMAGING SYSTEM AND METHOD FOR OCT IMAGING

TECHNICAL FIELD

The present invention essentially relates to a control system for optical coherence tomography (OCT) imaging means for imaging a subject, to a processing system and an OCT imaging system including such control system, and to a method for imaging a subject, using OCT.

BACKGROUND

Optical coherence tomography (in the following also called OCT, its typical abbreviation) is an imaging technique that uses low-coherence light to capture two- and three-dimensional images from within optical scattering media (e.g., biological tissue) with high resolution. It is, inter alia, used for medical imaging. Optical coherence tomography is based on low-coherence interferometry, typically employing near-infrared light. The use of relatively long wavelength light allows it to penetrate into the scattering medium. A medical field of particular interest for OCT is ophthalmology, a branch of medicine related to (in particular human) eyes and its disorders and related surgeries.

SUMMARY

According to the invention, a control system, a processing system, an OCT imaging system and a method for imaging a subject with the features of the independent claims are proposed. Advantageous further developments form the subject matter of the dependent claims and of the subsequent description.

The present invention relates to a control system for optical coherence tomography (OCT) imaging means for imaging a subject, in particular, for real-time imaging of the subject. This subject, preferably, includes or is an eye. The type of OCT to be used is, preferably, spectral domain OCT (also known as Fourier domain OCT), as will also be described later.

While spectral or Fourier domain OCT can be based on a broad band light source and a spectrometer system (e.g., with a diffraction grating or other dispersive detector), also swept-source OCT (SS-OCT) can be used, in which a frequency of the light is varied over time (i.e., a spectrally scanning system).

The control system is configured to control optical coherence tomography imaging means to scan the subject by means of optical coherence tomography for acquiring scan data or a scan data set. Data processing is performed on the scan data and includes, for example, DC or baseline removal, spectral filtering, wavenumber resampling, dispersion correction, Fourier transform, scaling, image filtering, and optionally additional image enhancement steps, in order to obtain image data for an image of the subject. Typically, a set of image data—or a frame (in the sense of a two-dimensional image, in particular, in live or real-time imaging)—is combined to a two-dimensional OCT image, a B-scan. The underlying scan data thus includes several spectra or A-scans.

In OCT, areas of the sample (subject) or tissue that reflect back a lot of light will create greater interference than areas that do not. Any light that is outside the short coherence length will not interfere. This reflectivity profile is called an A-scan and contains information about the spatial dimensions and location of structures within the sample or tissue. A cross-sectional tomograph, called B-scan, may be achieved by laterally combining a series of these axial depth scans (A-scan). The B-scan can then be used to create a two-dimensional OCT image to be viewed.

In particular, Fourier domain optical coherence tomography (FD-OCT) uses the principles of low-coherence interferometry to generate two- or three-dimensional images of a subject (sample). Light from a light source is split between a reference arm and a sample arm. A signal pattern at a detector is generated that is composed of the base light spectrum and modulated by interference from light between the reference arm and sample arm.

Typically, the two-dimensional image, with dimensions in x- and z-direction (where x is a lateral direction and z is an axial or depth direction, i.e., the direction of the OCT light beam entering the subject), is displayed in real-time to the end user. The detected position along the z-dimension (or axial direction) in space depends upon the difference in optical path length between the sample (subject) and reference beams. When imaging live samples, motion of the sample target along the axis of the probe beam results in the generated OCT image moving up or down along the z-axis (axial direction). This can result in a defocused image that causes loss of image quality and may even result in the image moving outside of the field of view entirely.

In order to stabilize the image and preserve image quality, the following technique is proposed within the present invention. The control system is configured to adapting at least one parameter of the OCT imaging means based on a change of a value, which characterizes an axial position of the subject with respect to the OCT imaging means, between two sets of image data. In order to obtain such value, the control system can be configured to determining the value (or a magnitude of such value) characterizing an axial position of the subject with respect to the OCT imaging means. This value can, in particular, be an absolute or relative measure of the axial or z-position, for example, measured in pixels within the OCT image. This allows tracking the axial motion of the subject.

Also, the control system can be configured to receive, from an external processing unit, such value. In this case, such (external) processing unit is configured to perform the steps: determining the value characterizing the axial position of the subject with respect to the OCT imaging means, and providing the value to the control system. The processing unit can be connected to the control system via communication means like Ethernet or the internet. In particular, the processing unit can be formed by a server or cloud computing system, what is of particular interest in special cases as will be described in the following. Also, such processing unit can be formed by a PC or other computer. The control system and the processing unit then can be considered as processing system.

The value can be obtained by, in particular, image processing methods or using an image metric, preferably, being based on a maximum and/or mean weighted signal strength. Also the use of machine learning methods is preferred, such machine learning method configured to identifying portions of the subject in the image data set A more detailed description of such methods will be provided later. In particular with machine learning methods (and also with image processing methods or metrics) the use of such external processing unit is of interest due to high computing power that can be provided in this way. Nevertheless, depending on the specific situation, such methods can also be performed on the control system.

Another possibility to obtain such value characterizing an axial position of the subject with respect to the OCT imaging means is the use of an external probe beam, e.g. from a laser, like from laser range finding (which might be based on time-of-flight principle).

As mentioned above, the control system is configured to adapting the at least one parameter of the OCT imaging means based on a change of the value between two sets of image data. Each set of image data, in particular, corresponds to a frame of an (OCT) image, for example, during live or real-time imaging. These parameters preferably are a focal position of a sample arm of the OCT imaging means, an axial position of a reference arm mirror (in the reference arm of the OCT imaging means), and an axial position of an objective of the sample arm (of the OCT imaging means). It is to be noted that it is typically sufficient to choose one out of the axial position of the reference arm reflector (or mirror) and the objective of the sample arm, as they typically have the same effect.

In this way, tracking the axial motion of the sample (subject) can be used in conjunction with dynamically adjusting the optical focus and reference arm positions and, thus, stabilize the image and preserve image quality.

In order to adjust the at least one parameter of the OCT means, the control can be configured to providing a signal for corresponding adapting means, which are configured to mechanically and/or digitally adapt, upon receiving the signal, the at least one parameter of the OCT imaging means. Such means can include a reference arm controller configured to vary the axial position of the reference arm reflector. Similar means can be provided for the sample arm, in particular, for the objective in order to adjust its focus or focal position. In this case, such means could be part of a microscope including the objective and being used for OCT. Such adapting means may be provided in an OCT imaging system anyway or may be added if necessary. Of course, the respective OCT imaging means (reference arm, objective, etc.) must allow the respective adaption.

By using a metric derived from the image in real-time, the sample's depth position can be computed and tracked from frame to frame. The metric—or, in general, the image processing method—may include the z-position of maximum signal, a mean-weighted z-position, or any other image derived quantity relating to sample location. This information can, for example, be fed to the reference arm controller that will mechanically adjust the position of the reference arm reflector to maintain the OCT image of the sample at the same relative depth prior to any sample movement. The same data can also be used to adjust the focal position of the sample arm, which is also controlled digitally. This should allow for optimum positioning of the sample within the imaging window while maintaining high quality imaging.

Machine learning algorithms can also be employed to detect specific features of interest in an image (or frame), similar to facial recognition. Machine learning may include the use of e.g. multi-layered (artificial) neural networks with, for example, convolutional, pooling, activation, fully-connected, normalization, and drop-out layers. Each layer may contain a sequence of weights and biases that govern their response to a given input image.

This allows the creation of a complex model whose weights can be trained repeatedly against a series of ground-truth (or reference) input data until the model sufficiently predicts the number of regions corresponding to the desired features and provides confidence scores about the strength of each prediction. For example, when using ground-truth or known input images (images with known position of the relevant features), based on a deviation between an current output of the neural network from a known and/or expected value, the weights and/or biases can be adapted.

Results from the model are then, preferably, filtered to ensure that only the correct number of features and feature types are detected. For example, neural networks can be trained to detect the specific center of retinal vision (i.e., the fovea) within an OCT image or volume and to distinguish this region from the optic nerve head. A priori knowledge of the sample target can, for example, be used to ensure that only a singular instance or the correct number of instances, of each feature is detected. Differences between the cornea, the anterior and/or posterior lens surfaces, and the corneal angle can also be determined to allow focusing and centering of the OCT probe beam on a specific area of interest. This will allow for similar access to z-position information for axial tracking and also enable targeted detection and even x-y tracking, i.e., tracking of the image data set or corresponding OCT image in both lateral directions. Also, adaption of the OCT imaging means (in particular in the sample arm) to such lateral position change can be provided.

Further aspects of the invention are directed to the machine learning method. One aspect is the training of such machine learning method or neural network as explained above. In this case, a processing unit can be provided that receives or obtains input data, performs training steps as mentioned, and provides or generators output data. For example, data is collected, manually labeled features of interest in the data, data is split into training/validation sets, augment datasets, and then the neural network model is trained, using modifying/re-training/deploying the model.

A further aspect is the application of such trained neural network or machine learning method as mentioned before, determining the value characterizing an axial position of the subject with respect to the OCT imaging means. In this case, a processing unit (like the external one mentioned above) can be provided that receives or obtains input data (the image data acquired by OCT), performs processing steps as mentioned (identifying features in the image data), and provides or generators output data (the value).

Machine learning may also be used to detect and segment specific layers of interest in an image (such as the corneal endothelial layer or inner retinal layers). Data from different image sources, such as OCT and concurrent video camera images may also be combined to provide complementary information for applications such as tool tracking during surgical operations to provide feedback for robotic-assisted surgery and to keep OCT imaging centered on the location of the tool. It is also possible to train the model to detect abnormalities such as the build-up of fluid pockets or the development of holes or tearing of tissue (in the subject).

Previous solutions, such as described in U.S. Pat. No. 7,349,098 B2, are applied to time domain OCT, which is an older generation version of OCT that required axial scanning of either the sample or reference arms. Current generation OCT, known the mentioned spectral domain or Fourier domain OCT, does not have this requirement and allows for much faster image acquisition rates. Also, adjusted of both reference arm and focus allows improved imaging quality, in particular, for real-time imaging. If the focus is not adjusted to match adjustments to the reference arm, the sample would be at a sub-optimal imaging plane.

Furthermore, for samples with a large structural extent over depth (e.g., anterior segment imaging), it can be challenging to automatically determine to correct location within the sample to track. Previous solutions were devised to specific use cases, such as retinal tracking, but may not be as effective for tracking of the cornea or other large samples. The same holds true for the machine learning methods for feature tracking. Also, previous solutions, such as described in US 2016/0040977 A1, being applied post processing cannot help to improve quality in live or real-time imaging.

The different preferred features mentioned above allow specific, preferred combinations or embodiments, some of which will be described in the following.

An embodiment provides image tracking via a comparative metric computed from the current image frame. For example, this may involve a weighted mean computation based on the strength of signal of the image or another numeric value to detect the z-position of a sample in one frame. This position is then compared to the next frame to determine the z-shift between frames. Information is then fed to a controller of the sample arm focus as well as the reference arm position to optimally adjust the image position.

Another embodiment provides image recognition via machine learning methods, which can be used to identify portions of the sample that are of interest along with their axial z-position. This would also allow for classification of each image and potential automated identification of features of interest (i.e., the macula in the eye, top of the cornea, tip of the lens, etc.). This would possibly allow for a more generalized z-tracking algorithm, the results of which would also be fed to a controller mechanism for the sample focus and reference arm positions.

Another embodiment provides z-tracking that can be performed using an external probe beam to the OCT system that is dedicated to computing the depth range of the sample (such as laser range finding). Information is similarly fed to the optical control mechanism.

Another embodiment provides z-tracking being computed using any of the above methods, instead of adjusting the reference arm, however, the sample arm objective can be adjusted to compensate for the axial motion of the target. This would allow complete compensation of any axial motion and would, typically, require digital control over the sample arm of the microscope or OCT imaging means.

The invention also relates to an optical coherence tomography (OCT) imaging system for (in particular, real-time) imaging a subject, e.g. an eye, comprising the control system according to the invention and as described above, and optical coherence tomography imaging means in order to perform the OCT scan (for a more detailed description of such OCT imaging means it is referred to the drawings and the corresponding description). Preferably, the OCT imaging system is configured to display an image of the subject on display means. Such display means can be part of the OCT imaging system. Preferably, the OCT imaging system further comprises means configured to mechanically and/or digitally adapt, upon receiving a signal, at least one of the following: a focal position of a sample arm, an axial position of a reference arm reflector, and an axial position of an objective of the sample arm. In addition, a probe configured to provide a probe beam in order to determine the value characterizing the axial position of the subject with respect to the OCT imaging means can be provided.

The invention also relates to a method for imaging a subject like an eye, using optical coherence tomography (OCT), preferably, spectral domain OCT (or also SS-OCT). The method comprises the following steps: acquiring scan data from the subject by means of optical coherence tomography, performing data processing on the scan data, and obtaining image data for an image of the subject, and determining a value characterizing an axial position of the subject with respect to the OCT imaging means. Further, the method comprises: adapting, based on a change of the value between two sets of image data, at least one parameter of the OCT imaging means.

The invention also relates to a computer program with a program code for performing a method according to the invention when the computer program is run on a processor, processing system or control system, in particular, like described before.

With respect to further preferred details and advantages of the OCT imaging system and the method, it is also referred to the remarks for the control system above, which apply here correspondingly.

Further advantages and embodiments of the invention will become apparent from the description and the appended figures.

It should be noted that the previously mentioned features and the features to be further described in the following are usable not only in the respectively indicated combination, but also in further combinations or taken alone, without departing from the scope of the present invention.

SHORT DESCRIPTION OF THE FIGURES

DETAILED DESCRIPTION

Figure 1:
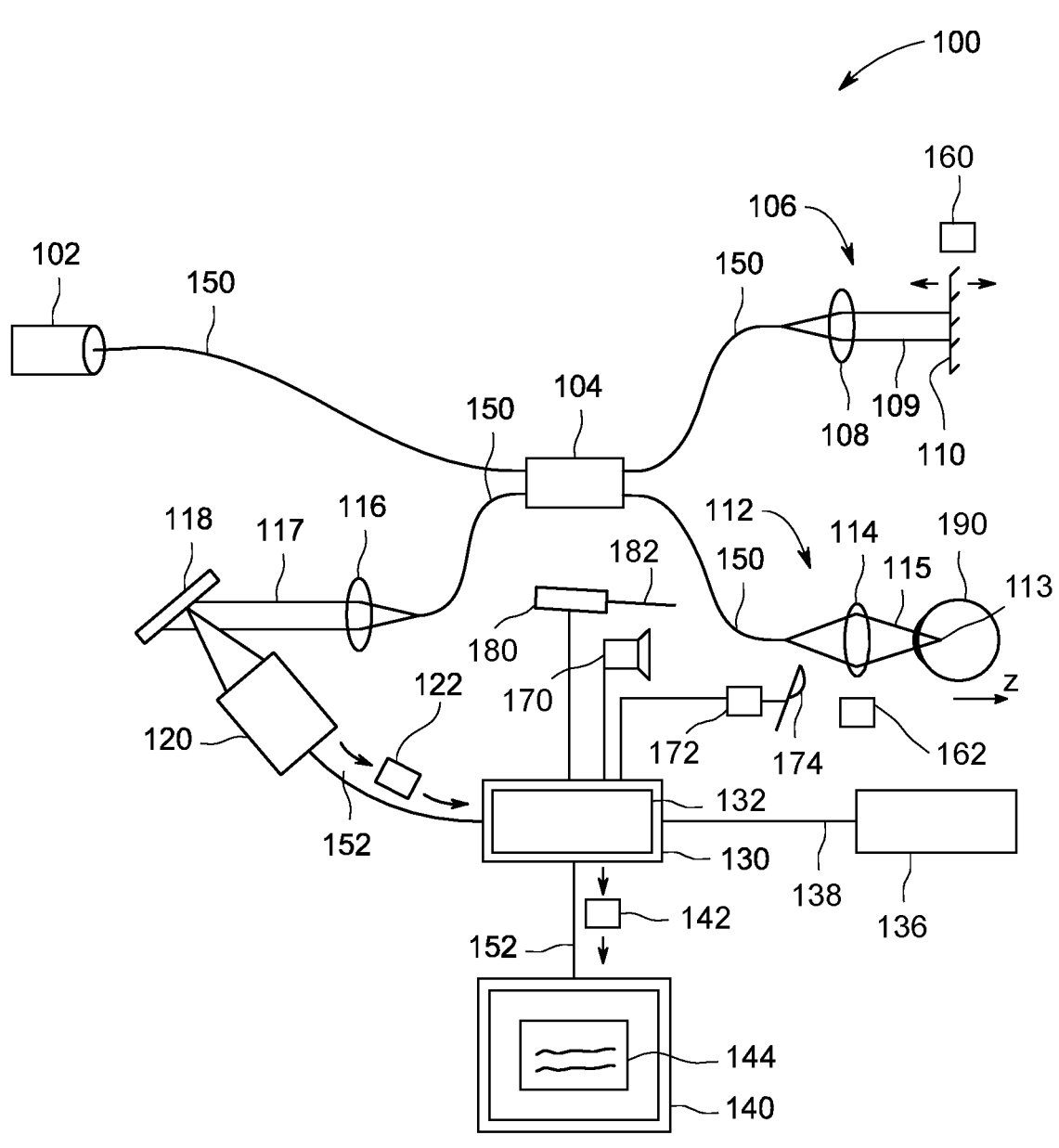
FIG. 1 shows a schematic overview of an OCT imaging system according to the invention in a preferred embodiment.

In FIG. 1, a schematic overview of an optical coherence tomography (OCT) imaging system 100 according to the invention in a preferred embodiment is shown. The OCT imaging system 100 comprises a light source 102 (e.g., a low coherence light source), a beam splitter 104, a reference arm 106, a sample arm 112, a diffraction grating 118, a detector 120 (e.g., a camera), a control system 130 and display means 140 (e.g., a display or monitor).

Light originating from the light source 102 is guided, e.g., via fiber optic cables 150, to the beam splitter 104 and a first part of the light is transmitted through the beam splitter 104 and is then guided, via optics 108 (which is only schematically shown and represented by a lens) in order to create a light beam 109 to a reference reflector or mirror 110, wherein the optics 106 and the reference mirror 110 are part of the reference arm 106. Adapting means 160 are provided and configured to adapt (digitally and/or mechanically) the axial position (it is indicated with arrows left and right of the mirror 110) of the mirror 110.

Light reflected from the reference mirror 110 is guided back to the beam splitter 104 and is transmitted through the beam splitter 104 and is then guided, via optics 116 (which is only schematically shown and represented by a lens) in order to create a light beam 117 to the diffraction grating 118.

A second part of the light, originating from the light source 102 and transmitted through the beam splitter 104 is guided via optics 114 (which is only schematically shown and represented by a lens) in order to create a light beam 115 (for scanning) to the subject 190 to be imaged, which, by means of example, is an eye. The optics 114 are part of the sample arm 112. In particular, optics 114 are used to focus the light beam 115 on a desired focal plane, i.e., the focal position, indicated with 113, can be set. The optics 114 also represent an objective (of, e.g., a microscope) used for the OCT. Adapting means 162 are provided and configured to adapt (digitally and/or mechanically) the focal position, e.g., by adapting the axial position of the optics 114.

Light reflected from the subject 190 or the tissue material therein is guided back to the beam splitter 104 and is transmitted through the beam splitter 104 and is then guided, via optics 116 to the diffraction grating 118. Thus, light reflected in the reference arm 106 and light reflected in the sample arm 112 are combined by means of the beam splitter 104 and are guided, e.g., via a fiber optic cable 150, and in a combined light beam 117 to the diffraction grating 118.

Light reaching the diffraction grating 118 is diffracted and captured by the detector 120. In this way, the detector 120, which acts as a spectrometer, creates or acquires scan data or scan data sets 122 that are transmitted, e.g., via an electrical cable 152, to the control system 130 comprising processing means (or a processor) 132. A scan data set 122 is then processed to obtain image data set 142 that is transmitted, e.g., via an electrical cable 152, to the display means 140 and displayed as a real-time image 144, i.e., an image that represents the currently scanned subject 190 in real-time. All the components except the control system and the display means can be considered as OCT imaging means.

In addition, an external probe 180 like a laser, providing a probe beam 182, is provided and connected to the control unit 130. It may be used to determine a z-direction of the subject 190 as will be described later.

Further, a processing unit 136 connected to the control system 130 via communication means 138 like Ethernet or internet (and a corresponding cable) is provided. As mentioned above, all relevant processing steps can be performed on the control system 130 (or its processing means 132). However, the step of determining the value, in particular by the machine learning method or the image metric, can also be performed on that external processing unit 136, which may have high computing power.

Further, another image source or imaging means 170 like a video camera, providing concurrent video camera images is provided. Such images may also be combined with the OCT images to provide complementary information for applications such as tool tracking during surgical operations to provide feedback for robotic-assisted surgery and to keep OCT imaging centered on the location of the tool. Exemplarily, a tool 174 and robotic means 172 for controlling and moving the tool 174 (e.g., a scalpel or a cutting laser) are shown. The robotic means 172 can be controlled by the control system, for example.

The process in which the intensity scan data set 122 is processed or converted to the image data set 142 that allows displaying of the scanned subject 190 on the display means 140 will be described in more detail in the following. In particular, an axial direction or z-direction, in which the subject 190 might move during observation (or a surgery), is indicated by reference numeral z.

Figure 2:
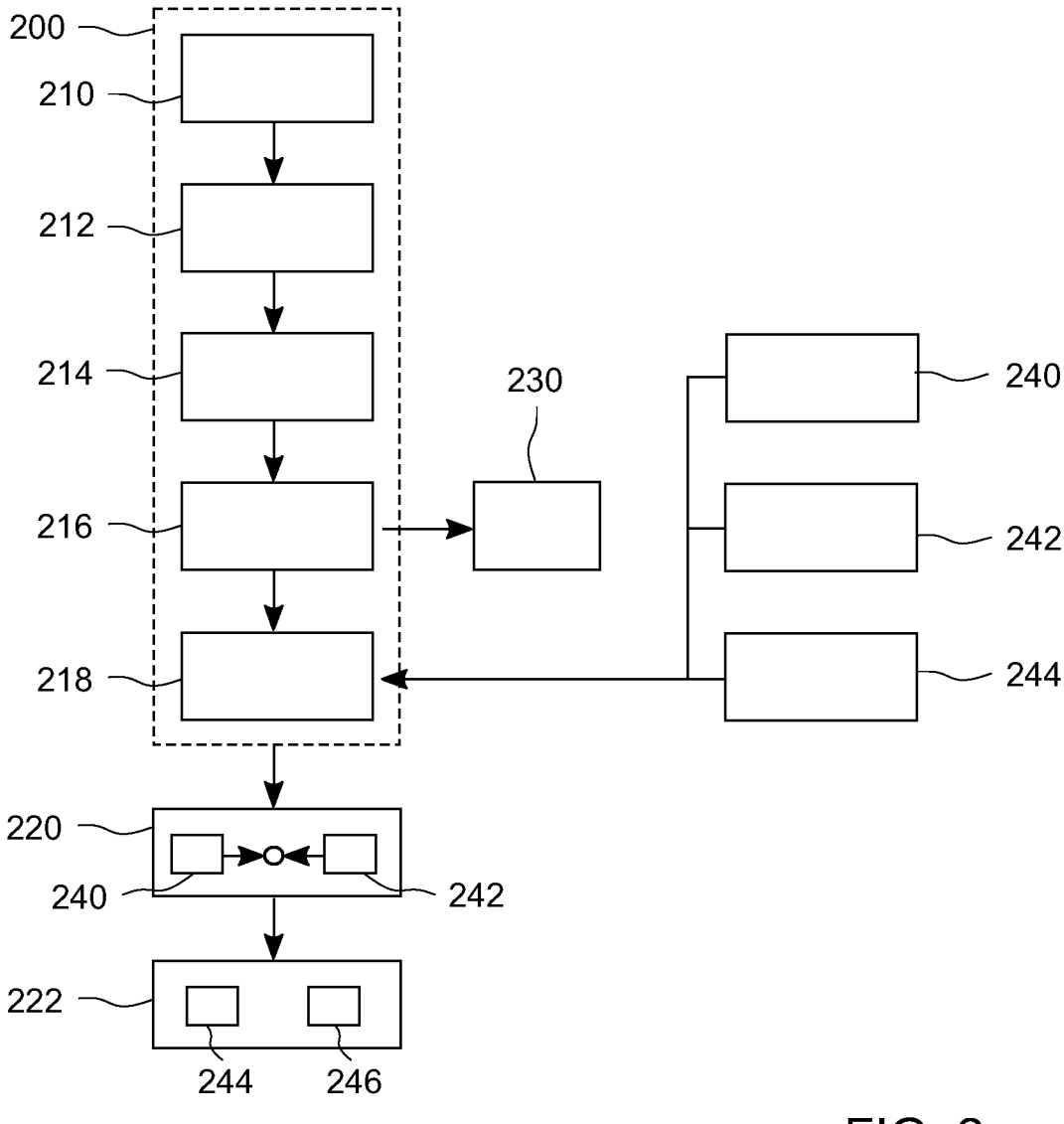
FIG. 2 shows, schematically, a flow scheme describing a method according to the invention in a preferred embodiment.

In FIG. 2, a flow scheme describing a method according to the invention in a preferred embodiment is shown schematically. For providing a real-time OCT image, scan data is acquired and image data is provided to be displayed as an image or OCT image on display means continually in, e.g., an imaging acquisition and processing process 200, and as described with respect to FIG. 1.

In step 210, scan data is acquired from the subject by means of optical coherence tomography, in step 212, the scan data is received at the control system and in step 214, data processing on the scan data is performed. Data processing step 214 can include, for example, DC or baseline removal, spectral filtering, wavenumber resampling, dispersion correction, Fourier transform, scaling, image filtering, and optionally additional image enhancement steps, in order to obtain, in step 216, image data for an image of the subject to be displayed. Such image data can be provided, in step 230, to the display means as mentioned with respect to FIG. 1 in order to provide real-time imaging.

Further, in step 218, a value characterizing an axial position of the subject with respect to the OCT imaging means is determined. It is to be noted that typically the OCT imaging means (see above) to not move in axial direction during a scan. Also, the sample arm or the optics 114 (e.g., the objective) may be considered as component with respect to which the axial direction is determined or measured. Such determination might be performed on a set of image data representing a frame or a two-dimensional OCT image. The value might be a relative z-position, for example, In FIG. 3, different OCT images 300, 302, 304 of a subject (in the example it is a retina of an eye) acquired by OCT at different points in time are shown. This example shows axial motion in z-direction during imaging of the retina. Each image frame or OCT image is acquired at a different time point, and movement of the eye causes the retina image to move up or down in the frame. The middle image 302, for example, moves out of focus and suffers a loss of signal.

As mentioned before, step 218 may be performed on the control system or on the external processing unit. In the latter case, the image data would have to be provided to the external processing unit and, after step 218, the value would have to be received from the control system.

Further, the method comprises, in a step 220, determining a potential change of the value between to, e.g., subsequent, image data sets or frames, two of such values indicated with 240 and 242. In case that a change that is determined is, for example, more than a specific threshold, two parameters 244, 246 of the OCT imaging means are adapted in step 222. For example, parameter 244 is a focal position of the sample arm, which is adapted by means 162 shown in FIG. 1. Parameter 246 can be an axial position of the reference arm reflector or mirror, which is adapted by means 160 shown in FIG. 1.

Figures 3, 4, 5:
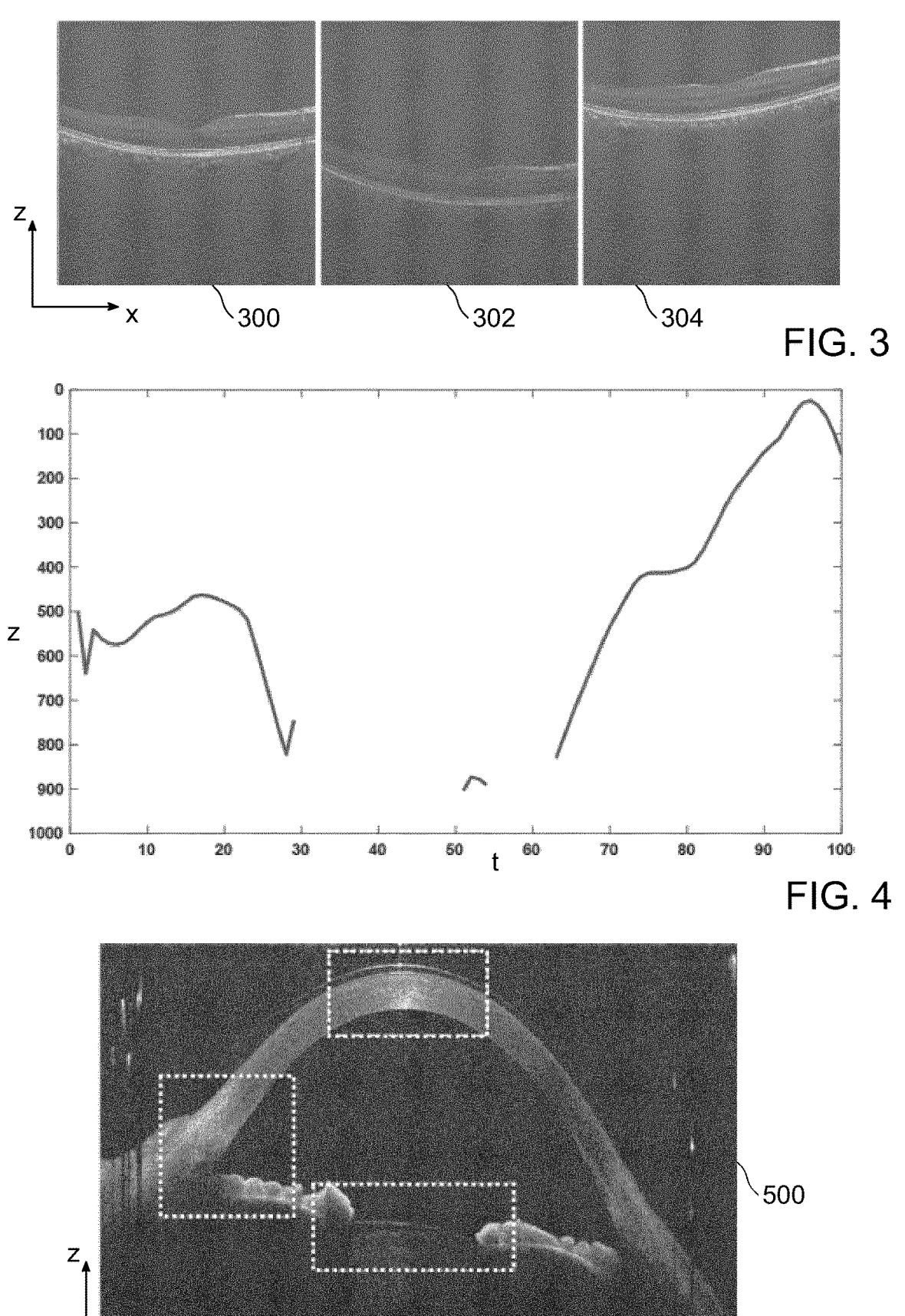
FIG. 3 shows, schematically, different OCT images of a subject acquired by OCT at different points in time.
FIG. 4 shows a diagram with variation of axial position of a subject over time.
FIG. 5 shows an OCT image with specific features indicated.

In this way, axial movement of the subject can be compensated. In FIG. 4, a diagram shows a variation of axial position of a subject over time. The z-direction is shown in pixels of an image and time t is shown in frame numbers. This example, in particular, shows tracking the z-position of the maximum brightness in each image over 100 frames. Frames that do not have a depth pixel have had the image move outside of the field of view.

As described above, the value characterizing the axial position of the subject with respect to the OCT imaging means can be determined (see step 218) in different ways. For example, an image metric 250 can be used looking for the maximum brightness in each image as mentioned for FIG. 4. Also, a machine learning method 260 can be used, looking for specific features in the OCT image.

In FIG. 5, an OCT image 500 is shown, with specific features indicated in boxes drawn with white dotted lines. This visualizes a concept of image recognition in OCT, using machine learning algorithms that can be trained to detect different features within an image. This yields information on the location of each feature and can assist with targeted z-tracking as well as directed scanning of specific regions of interest.

In FIG. 5, the uppermost whit box indicates a cornea of an eye, the lowermost white box indicates a lens of the eye, and the left white box indicates an angle between the cornea and the lens.

Besides such digital methods, also an external probe beam can be directed, in a step 270, onto the subject in order to obtain or determine a value indicative for the axial direction of the subject.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

Some embodiments relate to an OCT imaging system comprising a control system as described in connection with one or more of the FIGS. 1 to 5. Alternatively, an OCT imaging system may be part of or connected to a system as described in connection with one or more of the FIGS. 1 to 5. FIG. 1 shows a schematic illustration of an OCT imaging system 100 configured to perform a method described herein. The OCT imaging system 100 comprises an OCT imaging means and a computer or control system 130. The OCT imaging means are configured to take images and are connected to the control system 130. The control system 130 is configured to execute at least a part of a method described herein. The control system 130 may be configured to execute a machine learning algorithm. The control system 130 and (parts of) OCT imaging means may be separate entities but can also be integrated together in one common housing. The control system 130 may be part of a central processing system of the OCT imaging system 100 and/or the control system 130 may be part of a subcomponent of the OCT imaging system 100, such as a sensor, an actor, a camera or an illumination unit, etc. of the OCT imaging system 100.

The control system 130 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The control system 130 may comprise any circuit or combination of circuits. In one embodiment, the control system 130 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the control system 130 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The control system 130 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The control system 130 may also include a display device, one or more speakers, and a keyboard and/or controller, which can include a mouse, trackball, touch screen, voice-recognition device, or any other device that permits a system user to input information into and receive information from the control system 130.

Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

Embodiments may be based on using a machine-learning model or machine-learning algorithm. Machine learning may refer to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. For example, the content of images may be analyzed using a machine-learning model or using a machine-learning algorithm. In order for the machine-learning model to analyze the content of an image, the machine-learning model may be trained using training images as input and training content information as output By training the machine-learning model with a large number of training images and/or training sequences (e.g. words or sentences) and associated training content information (e.g. labels or annotations), the machine-learning model "learns" to recognize the content of the images, so the content of images that are not included in the training data can be recognized using the machine-learning model. The same principle may be used for other kinds of sensor data as well: By training a machine-learning model using training sensor data and a desired output, the machine-learning model "learns" a transformation between the sensor data and the output, which can be used to provide an output based on non-training sensor data provided to the machine-learning model. The provided data (e.g. sensor data, meta data and/or image data) may be preprocessed to obtain a feature vector, which is used as input to the machine-learning model.

Machine-learning models may be trained using training input data. The examples specified above use a training method called "supervised learning". In supervised learning, the machine-learning model is trained using a plurality of training samples, wherein each sample may comprise a plurality of input data values, and a plurality of desired output values, i.e. each training sample is associated with a desired output value. By specifying both training samples and desired output values, the machine-learning model "learns" which output value to provide based on an input sample that is similar to the samples provided during the training. Apart from supervised learning, semi-supervised learning may be used. In semi-supervised learning, some of the training samples lack a corresponding desired output value. Supervised learning may be based on a supervised learning algorithm (e.g. a classification algorithm, a regression algorithm or a similarity learning algorithm. Classification algorithms may be used when the outputs are restricted to a limited set of values (categorical variables), i.e. the input is classified to one of the limited set of values. Regression algorithms may be used when the outputs may have any numerical value (within a range). Similarity learning algorithms may be similar to both classification and regression algorithms but are based on learning from examples using a similarity function that measures how similar or related two objects are. Apart from supervised or semi-supervised learning, unsupervised learning may be used to train the machine-learning model. In unsupervised learning (only) input data might be supplied and an unsupervised learning algorithm may be used to find structure in the input data (e.g. by grouping or clustering the input data, finding commonalities in the data). Clustering is the assignment of input data comprising a plurality of input values into subsets (clusters) so that input values within the same cluster are similar according to one or more (pre-defined) similarity criteria, while being dissimilar to input values that are included in other clusters.

Reinforcement learning is a third group of machine-learning algorithms. In other words, reinforcement learning may be used to train the machine-learning model. In reinforcement learning, one or more software actors (called "software agents") are trained to take actions in an environment Based on the taken actions, a reward is calculated. Reinforcement learning is based on training the one or more software agents to choose the actions such, that the cumulative reward is increased, leading to software agents that become better at the task they are given (as evidenced by increasing rewards).

Furthermore, some techniques may be applied to some of the machine-learning algorithms. For example, feature learning may be used. In other words, the machine-learning model may at least partially be trained using feature learning, and/or the machine-learning algorithm may comprise a feature learning component Feature learning algorithms, which may be called representation learning algorithms, may preserve the information in their input but also transform it in a way that makes it useful, often as a preprocessing step before performing classification or predictions. Feature learning may be based on principal components analysis or cluster analysis, for example.

In some examples, anomaly detection (i.e. outlier detection) may be used, which is aimed at providing an identification of input values that raise suspicions by differing significantly from the majority of input or training data. In other words, the machine-learning model may at least partially be trained using anomaly detection, and/or the machine-learning algorithm may comprise an anomaly detection component.

In some examples, the machine-learning algorithm may use a decision tree as a predictive model. In other words, the machine-learning model may be based on a decision tree. In a decision tree, observations about an item (e.g. a set of input values) may be represented by the branches of the decision tree, and an output value corresponding to the item may be represented by the leaves of the decision tree. Decision trees may support both discrete values and continuous values as output values. If discrete values are used, the decision tree may be denoted a classification tree, if continuous values are used, the decision tree may be denoted a regression tree.

Association rules are a further technique that may be used in machine-learning algorithms. In other words, the machine-learning model may be based on one or more association rules. Association rules are created by identifying relationships between variables in large amounts of data. The machine-learning algorithm may identify and/or utilize one or more relational rules that represent the knowledge that is derived from the data. The rules may e.g. be used to store, manipulate or apply the knowledge.

Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge (e.g. based on the training performed by the machine-learning algorithm). In embodiments, the usage of a machine-learning algorithm may imply the usage of an underlying machine-learning model (or of a plurality of underlying machine-learning models). The usage of a machine-learning model may imply that the machine-learning model and/or the data structure/set of rules that is the machine-learning model is trained by a machine-learning algorithm.

For example, the machine-learning model may be an artificial neural network (ANN). ANNs are systems that are inspired by biological neural networks, such as can be found in a retina or a brain. ANNs comprise a plurality of interconnected nodes and a plurality of connections, so-called edges, between the nodes. There are usually three types of nodes, input nodes that receiving input values, hidden nodes that are (only) connected to other nodes, and output nodes that provide output values. Each node may represent an artificial neuron. Each edge may transmit information, from one node to another. The output of a node may be defined as a (non-linear) function of its inputs (e.g. of the sum of its inputs). The inputs of a node may be used in the function based on a "weight" of the edge or of the node that provides the input. The weight of nodes and/or of edges may be adjusted in the learning process. In other words, the training of an artificial neural network may comprise adjusting the weights of the nodes and/or edges of the artificial neural network, i.e. to achieve a desired output for a given input.

Alternatively, the machine-learning model may be a support vector machine, a random forest model or a gradient boosting model. Support vector machines (i.e. support vector networks) are supervised learning models with associated learning algorithms that may be used to analyze data (e.g. in classification or regression analysis). Support vector machines may be trained by providing an input with a plurality of training input values that belong to one of two categories. The support vector machine may be trained to assign a new input value to one of the two categories. Alternatively, the machine-learning model may be a Bayesian network, which is a probabilistic directed acyclic graphical model. A Bayesian network may represent a set of random variables and their conditional dependencies using a directed acyclic graph. Alternatively, the machine-learning model may be based on a genetic algorithm, which is a search algorithm and heuristic technique that mimics the process of natural selection.

LIST OF REFERENCE SIGNS

100 OCT imaging system
102 light source
104 beam splitter
106 reference arm
108, 114, 116 optics

14

109, 115, 117 light beams
110 reference mirror
112 sample arm
113 focal position
118 diffraction grating
120 detector
122 intensity scan data
130 control system
132 processing means
136 processing unit
138 communication means
140 display means
142 image data set
150 fiber optic cable
152 electrical cable
160, 162 adapting means
170 video camera
172 tool
174 robotic means
180 external probe
182 external probe beam
190 subject
x, z directions
t time
200-230, 270 method steps
240, 242 values
244, 266 parameters
250 imaging metric
260 machine learning method
300-304, 500 OCT images

The invention claimed is:

1. A control system for controlling optical coherence tomography (OCT) imaging means for imaging a subject, the control system being configured to:
   receive scan data from the subject, the scan data being acquired by the OCT imaging means,
   perform data processing on the scan data,
   obtain image data for an image of the subject based on the data processing on the scan data, and
   adapt at least one parameter of the OCT imaging means based on a change of a value between two sets of the image data, wherein the two sets of the image data correspond to the scan data acquired by the OCT imaging means at two sequential times, and wherein the value characterizes an axial position of the subject with respect to the OCT imaging means at each respective time of the two sequential times.

2. The control system of claim 1, wherein the at least one parameter of the OCT imaging means is selected from the group consisting of a focal position of a sample arm, an axial position of a reference arm reflector, and an axial position of an objective of the sample arm.

3. The control system of claim 1, being configured to adapt the at least one parameter of the OCT imaging means by providing a signal for corresponding adapting means, which are configured to
   mechanically and/or digitally adapt, upon receiving the signal, the at least one parameter of the OCT imaging means.

4. The control system of claim 1, wherein the scan data from the subject is acquired by spectral domain optical coherence tomography.

5. The control system of claim 1, further being configured to determine the value characterizing the axial position of the subject with respect to the OCT imaging means.

6. The control system of claim 5, being configured to determine, from the image data, the value characterizing the axial position of the subject with respect to the OCT imaging means, by a machine learning method configured to identify portions of the subject in each respective set of the image data.

7. The control system of claim 5, being configured to determine, from the image data, the value characterizing the axial position of the subject with respect to the OCT imaging means, by using an image metric based on a maximum signal strength and/or a mean weighted signal strength.

8. A processing system for optical coherence tomography imaging means, the processing system comprising:

the control system of claim 1, and a processing unit configured to determine the value characterizing the axial position of the subject with respect to the OCT imaging means, and providing the value to the control system.

9. An optical coherence tomography imaging system for imaging a subject, comprising the control system of claim 1, and the optical coherence tomography imaging means.

10. The optical coherence tomography imaging system of claim 9, the optical coherence tomography means comprising a sample arm including an objective and, a reference arm including a reference arm reflector, the optical coherence tomography imaging system further comprising adapting means configured to mechanically and/or digitally adapt, upon receiving a signal, at least one of: a focal position of the sample arm, an axial position of the reference arm reflector, or an axial position of an objective of the sample arm.

11. The optical coherence tomography imaging system of claim 9, configured for use during a surgical procedure being performed on the subject.

12. A method for imaging a subject using an optical coherence tomography imaging system, the method comprising:

acquiring scan data from the subject by using the optical coherence tomography imaging system, performing data processing on the scan data, obtaining image data for an image of the subject based on the data processing on the scan data, determining a value characterizing an axial position of the subject with respect to the OCT imaging system, and adapting at least one parameter of the OCT imaging system based on a change of the value between two sets of the image data, wherein the two sets of the image data correspond to the scan data by the OCT imaging system at two sequential times.

13. The method of claim 12, wherein the at least one parameter of the OCT imaging system is selected from the group consisting of: a focal position of a sample arm, an axial position of a reference arm reflector, and an axial position of an objective of the sample arm.

14. The method of claim 12, wherein the value characterizing the axial position of the subject with respect to the OCT imaging system is determined by at least one of:

an image metric based on a maximum signal strength and/or a mean weighted signal strength, or a machine learning method configured to identify portions of the subject in the image data.

15. A non-transitory computer-readable medium comprising a program code that when the program code is executed on a processor, a computer, or a programmable hardware component causes the processor, the computer, or the programmable hardware component to perform the method of claim 12.

* * * * *